US010337996B2

(12) United States Patent
Blagojevic et al.

(10) Patent No.: US 10,337,996 B2
(45) Date of Patent: Jul. 2, 2019

(54) LIDAR INSTRUMENT AND METHOD OF OPERATION

(71) Applicant: The United States of America as represented by the Administrator of the National Aeronautics and Space Administration, Washington, DC (US)

(72) Inventors: Branimir Blagojevic, Ellicott City, MD (US); Melissa Trainer, Silver Spring, MD (US); Alexander Pavlov, Crofton, MD (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 15/247,281

(22) Filed: Aug. 25, 2016

(65) Prior Publication Data

US 2018/0059023 A1 Mar. 1, 2018

(51) Int. Cl.
| | |
|---|---|
| *G01S 17/88* | (2006.01) |
| *G01N 21/64* | (2006.01) |
| *G01S 7/481* | (2006.01) |
| *G01N 15/14* | (2006.01) |
| *B64G 1/66* | (2006.01) |

(52) U.S. Cl.

CPC .......... *G01N 21/6486* (2013.01); *B64G 1/66* (2013.01); *G01N 15/1429* (2013.01); *G01S 7/4813* (2013.01); *G01S 17/88* (2013.01); *G01N 2015/1493* (2013.01)

(58) Field of Classification Search
CPC .......... G01S 7/4813; G01N 2021/4709; G01N 2021/1795; G01N 15/0205; G01N 21/6486; B64G 1/1021
See application file for complete search history.

(56) References Cited

U.S. PATENT DOCUMENTS

| | | | | |
|---|---|---|---|---|
| 2006/0231771 A1* | 10/2006 | Lee | G01N 21/645 250/458.1 |
| 2010/0034222 A1* | 2/2010 | Richard | G01S 7/4814 372/18 |

* cited by examiner

*Primary Examiner* — David Porta
*Assistant Examiner* — Faye Boosalis
(74) *Attorney, Agent, or Firm* — Christopher O. Edwards; Bryan A. Geurts; Mark P. Dvorscak

(57) ABSTRACT

The present invention relates to a Lidar surveying instrument, which is capable of detecting and discriminating laser-induced particle fluorescence of any biological or non-biological atmospheric particles. The present astrobiology sensing instrument can remotely sense and discriminate, in real-time, the bio-indicator aerosol material signatures and environmental interferents that exist in an extraterrestrial environment, such as Mars, in order to expand the search for signatures of extraterrestrial life from the planetary soil to the planetary ground level atmosphere, by performing atmospheric volume scans of hundreds of meters in a radial direction around a planetary vehicle or a spacecraft. The Lidar instrument technology of the present invention employs real-time aerosol particle detection and discrimination based on two physical variables: particle fluorescence and particle size in the bio-discrimination space.

18 Claims, 4 Drawing Sheets

LIDAR INSTRUMENT AND METHOD OF OPERATION

BACKGROUND OF THE INVENTION

1. Field of the Invention

The present invention relates to a Lidar (laser or light detection and ranging) surveying instrument, which is capable of detecting and discriminating laser-induced particle fluorescence, and particle size, of any biological or non-biological atmospheric particles.

2. Description of the Related Art

Previous Lidar methods have been in the form of a pulsed laser to measure ranges of distances on Earth. The light pulses, combined with other data recording devices, generate precise, three-dimensional information about the shape of the Earth and its surface characteristics. Lidar is used to produce more accurate shoreline maps, make digital elevation models for use in geographic information systems, to assist in emergency response operations, and other applications.

Lidar has also been used in space to measure the Earth's cloud cover and track various kinds of particles in the atmosphere. Light is reflected from tiny particles in the atmosphere, back to a telescope aligned with the laser of the Lidar instrument. By precisely timing the Lidar "echo", and by measuring how much laser light is received by the telescope, the location, distribution, and nature of the particles can be determined. Thus, atmospheric constituents from cloud droplets to industrial pollutants can be detected.

However, the use of Lidar extra-terrestrially, has not been envisaged, particularly the use of Lidar to detect life on other planets, such as Mars, where aerosol extinction (i.e., the measure of attenuation of light passing through the atmosphere due to scattering and absorption of aerosol particles) is about two orders of magnitude higher than for the Earth's atmosphere due to micron-size dust aerosol particles.

SUMMARY OF THE INVENTION

The present invention relates to a Lidar (laser or light detection and ranging) surveying instrument, which is capable of detecting and discriminating laser-induced particle fluorescence, and particle size, of any biological or non-biological atmospheric particles.

In one embodiment, the present invention relates to a novel astrobiology sensing instrument, which can remotely sense and discriminate, in real-time, the bio-indicator aerosol material signatures and environmental interferents that exist in an extraterrestrial environment, such as Mars. In one embodiment, the present invention would expand the search for signatures of extraterrestrial life from, for example, the planetary soil, to the planetary ground level atmosphere, by performing atmospheric volume scans of hundreds of meters in a radial direction around a planetary vehicle or a spacecraft (e.g., rover or lander). The Lidar instrument technology of the present invention employs real-time aerosol particle detection and discrimination based on two physical variables: particle fluorescence and particle size, in the bio-discrimination space.

In one embodiment the Lidar instrument of the present invention detects a biological signature or a non-biological signature in an extraterrestrial environment, including: a transceiver having a plurality of lasers operating at 266 nm, 355 nm, and 905 nm wavelengths, and emitting laser beams at an aerosol cloud of particles in the extraterrestrial environment; and a plurality of telescopes coupled to instrument optics using optical fibers, and connected to a plurality of detectors; wherein the laser beams excite the aerosol cloud to induce fluorescence and cause differential-wavelength elastic backscatter which produces data which is measured in real-time by the detectors to determine a type of material from the biological or non-biological signature of each of the particles, and a particle size of each of the particles.

In one embodiment, the detectors are photon-counting modules in both an ultraviolet wavelength range and a near-infrared wavelength range; and each of the 266 nm laser and the 355 nm laser includes a filter and a photo multiplier tube; and a filter and an avalanche photodiode are disposed with the 905 nm laser.

In one embodiment, an alert is issued to a user in real-time on condition that said type of material of each of the particles indicates a predetermined biological or non-biological signature.

In one embodiment, the particle size and the type of material of each of the particles is determined by making comparisons of the data received on fluorescence, with a computer database containing biological and non-biological or environmental parameters.

In one embodiment, the Lidar instrument operates at one of ground level or from space on a fly-by mission through the aerosol cloud.

In one embodiment, the environmental parameters are ground level environmental parameters of an atmosphere of the extraterrestrial environment, and include Kaolin clay and JSC Mars 1a.

In one embodiment, the Lidar instrument includes a plurality of operational modes, including a scanning mode, and a staring mode; wherein the scanning mode is for high-fluorescence yield of bio-indicator particle detection; and wherein the staring mode is used for low-fluorescence yield dust particle detection.

In one embodiment, the Lidar instrument is operated at one of night, during sunset, or during sunrise without looking at the Sun, or at a shaded landscape as a hard target.

In one embodiment, a signal-to-noise (S/N) performance of the Lidar instrument is higher than 1.

In one embodiment, the Lidar instrument is configured to fit in a planetary vehicle or a spacecraft.

In one embodiment, a method of detecting a biological signature or a non-biological signature in an extraterrestrial environment using Lidar, includes: emitting a laser beam from a transceiver having a plurality of lasers operating at 266 nm, 355 nm, and 905 nm wavelengths, into an aerosol cloud of particles in the extraterrestrial environment; and providing a plurality of telescopes coupled to instrument optics using optical fibers and connected to a plurality of detectors; wherein the laser beams excite the aerosol cloud to induce fluorescence and cause differential-wavelength elastic backscatter which produces data which is measured in real-time by the detectors to determine a type of material from the biological or non-biological signature of each of the particles, and a particle size of each of the particles.

In one embodiment, the method includes issuing an alert to a user in real-time on condition that the type of material of each of the particles indicates a predetermined biological or non-biological signature.

In one embodiment, the method includes making comparisons of the data received on fluorescence, with a computer database containing biological and non-biological or environmental parameters, in order to determine the particle size and the type of material of each of the particles.

Thus has been outlined, some features consistent with the present invention in order that the detailed description thereof that follows may be better understood, and in order that the present contribution to the art may be better appreciated. There are, of course, additional features consistent with the present invention that will be described below and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

DESCRIPTION OF THE INVENTION

Figure 1:
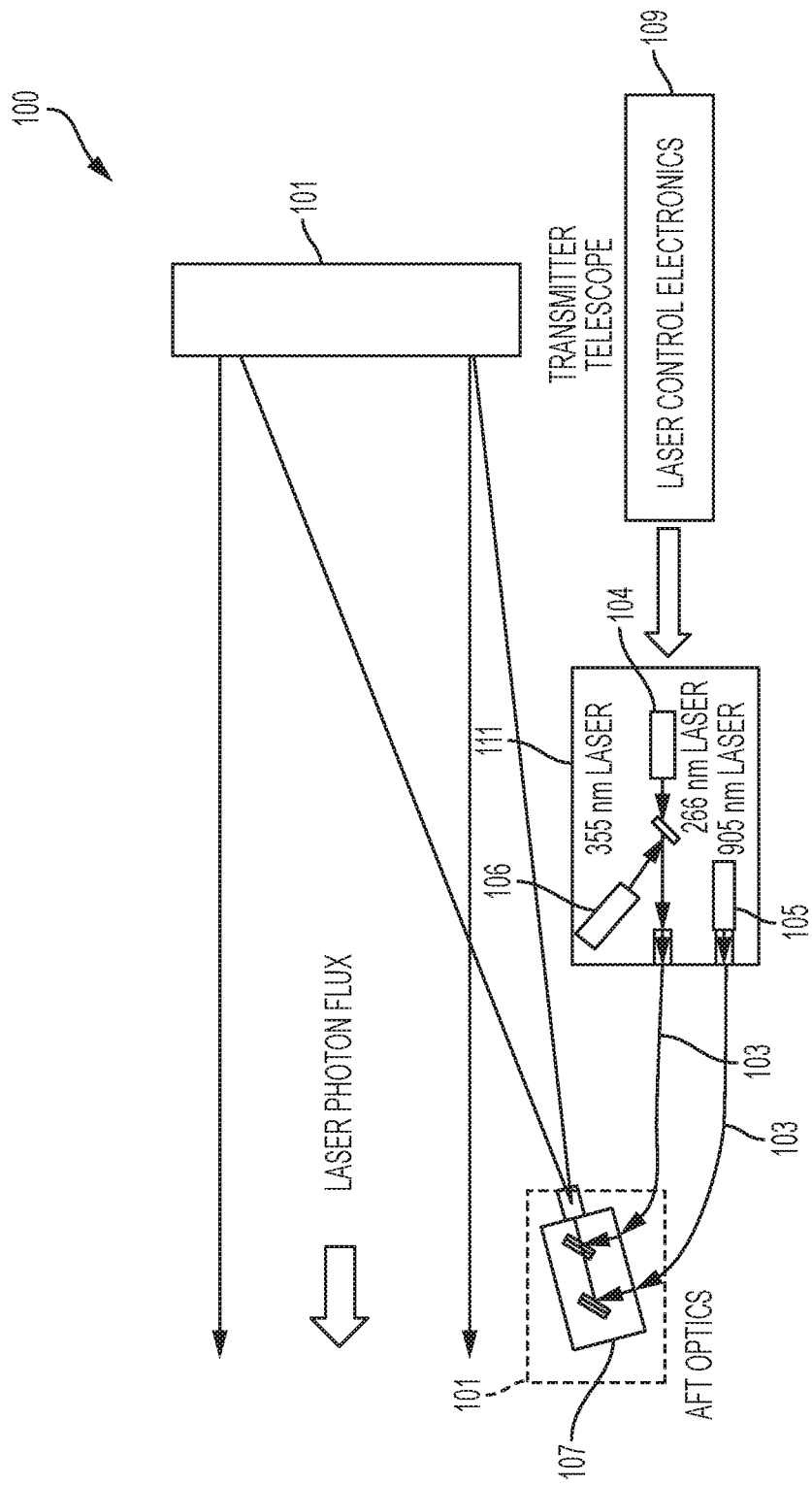
FIG. 1 is a schematic diagram of the transmission optics and lasers of a Lidar instrument, according to one embodiment consistent with the present invention.
Figure 2:
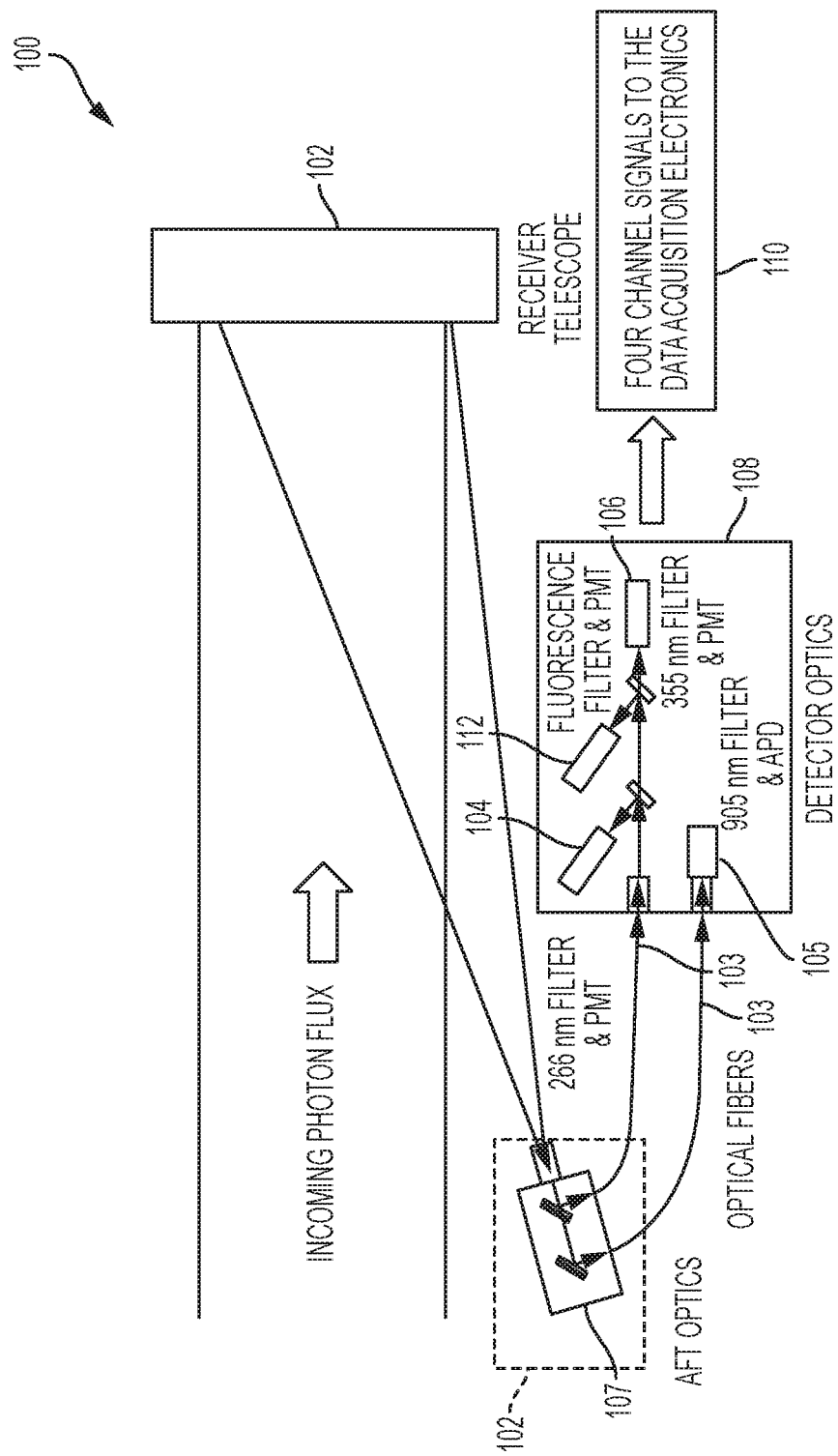
FIG. 2 is a schematic diagram of the receiver optics and detectors of a Lidar instrument, according to one embodiment consistent with the present invention.
Figure 3:
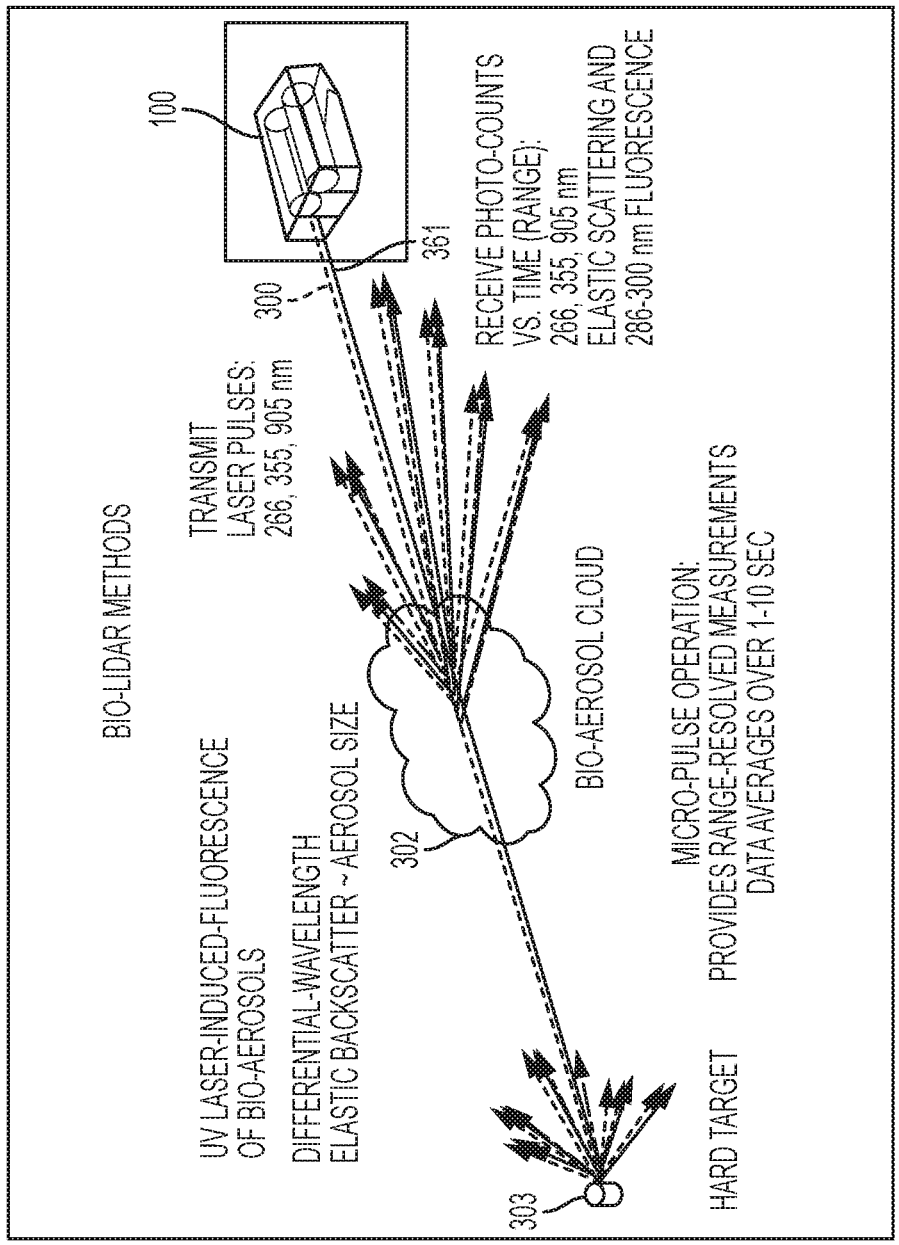
FIG. 3 is a schematic diagram of the Lidar instrument in use, according to one embodiment consistent with the present invention.

The present invention relates to a Lidar (laser or light detection and ranging) surveying instrument, which is capable of detecting and discriminating laser-induced particle fluorescence, and particle size, of any biological or non-biological atmospheric particles.

In one embodiment, the present invention relates to a novel astrobiology sensing instrument, which can remotely sense and discriminate, in real-time, the bio-indicator aerosol material signatures and environmental interferents that exist in an extraterrestrial environment, such as Mars. In one embodiment, the astrobiology sensing instrument of the present invention would expand the search for signatures of extraterrestrial life from the planetary soil, for example, to the planetary ground level atmosphere, by performing atmospheric volume scans of hundreds of meters in a radial direction around a planetary vehicle or a spacecraft (e.g., rover or lander). In one embodiment, the bio-Indicator Lidar technology of the present invention employs real-time aerosol particle detection and discrimination based on two physical variables: particle fluorescence and particle size in the bio-discrimination space.

In one embodiment, the Lidar instrument 100 of the present invention (see FIGS. 1-2) includes: a transceiver containing two sets of telescopes 101, 102 and fiber coupling optics 103 thereto; and a laser transmitter 111 containing, at a minimum, two lasers 104, 105 emitting laser beams or lines (i.e., 266 nm and 905 nm, respectively) 300, 361 (see FIG. 3), which are pulse-operated (i.e., 1 Hz) at low repetition rates. The lasers 104-105 are produced on solid state technology and compatible with space flight requirements, including low (~1 W) power consumption (the only consumable), and low weight.

In one embodiment with respect to extraterritorial operation, in addition to the 266 nm fluorescence excitation laser 104, a 355 nm laser presence 106 is necessary for successful bio-indicator discrimination due to significant Lidar elastic signal return loss caused by the high aerosol extinction of dust particles extra-terrestrially (i.e., on Mars).

In one embodiment, telescope 101 transmits all the laser beams 300, 301 (see FIG. 3) via optics 107 (including coupling lenses and beam splitter/combiner group known in the art) (see FIG. 1), and the second telescope 102 receives Lidar signals from the atmosphere (see FIG. 2). In one embodiment, the telescopes 101, 102 are fiber-coupled using optical fibers 103 to the lasers 104, 105, and detectors 108. In one embodiment, the laser transmitter 111 is connected to laser control electronics 109, and the detectors 108 are connected to data and communication electronics 110 (see FIGS. 1-2). A power supply provides power to the electronics 109, 110 (now shown).

In one embodiment, the detectors 108 are photon-counting modules in both the ultraviolet (UV) (i.e., 266 nm and 355 nm) and near-infrared (i.e., 905 nm) wavelength ranges (see FIG. 2). Filters are disposed with photo multiplication tubes (PMTs) for the 266 nm laser and 355 nm laser, for the fluorescence channel 112. A filter and avalanche photodiode is used with the 905 nm laser. In one embodiment, the fluorescence channel 112 detects the fluorescence from the biological or non-biological target in a narrow band of 286 to 300 nm wavelengths.

On-board processing of data is accomplished with the Lidar instrument 100, and communication is performed via a network controller of the data and communication electronics 110.

Note that the extraterrestrial signal-to-noise (S/N) performance, for example on Mars, is higher than 1, which is similar to Earth ground atmosphere due to two orders of magnitude higher aerosol extinction vs. Earth, and low molecular atmospheric extinction due to Raleigh scattering.

In one embodiment, the Lidar instrument 100 of the present invention is designed to fit in existing locations of an existing terrestrial vehicle or spacecraft (e.g., rover or lander). In one embodiment, the Lidar instrument 100 is designed to operate at ground or terrestrial level.

In one embodiment, the Lidar instrument 100 of the present invention is aimed at a hard target 303 (i.e., end of the laser optical path, like a knoll, hill or mountain) in a discrimination space extra-terrestrially, and the lasers 104-105 emit laser pulses 300, 301, respectively, to excite an aerosol cloud 302, containing biological particles, non-biological particles or environmental particles. The UV laser excitation of the aerosol cloud 302 induces fluorescence, and causes differential-wavelength elastic backscatter which is measured to determine particle size and the biological or non-biological signatures indicating particular particle materials. In particular, the detectors 108 of the Lidar instrument 100 of the present invention can receive photo-counts vs. time (range) at 266, 355, and 905 nm elastic scattering and 286-300 nm fluorescence.

In one embodiment, due to the high 266 nm excited, induced fluorescence yield of all bio-signature types, the bio-indicator aerosol discrimination capabilities are superior in comparison to all other 355 nm or 532 nm excitation bio-Lidar types.

In one embodiment, the Lidar instrument 100 of the present invention includes a plurality of operational modes, namely, a scanning mode or a staring mode.

In one embodiment, the staring mode is used for low-fluorescence yield dust particle detection (i.e., taking minute(s) of integration time to provide range-resolved measurement data averages). In one embodiment, the scanning mode is for high-fluorescence yield of bio-indicator particle detection (i.e., a fraction of minute integration time to provide range-resolved measurement data averages, usually 1-10 seconds).

In one embodiment, the operation of the Lidar instrument 100 of the present invention is performed either at night, during sunset or sunrise (no direct looking at the Sun), or at a shaded landscape hard target (i.e., hills, mountains, recurring slope lineae, etc.).

In one embodiment, the data electronics 110 of the Lidar instrument 100 of the present invention utilizes a computer software program which processes the Lidar signals and runs analysis algorithms of the data received by the detectors 108 in real-time. In one embodiment, the computer processor of the data electronics 110 analyzes the data received on the fluorescence to determine particle size, by making comparisons with a computer database containing various location ground level biological, non-biological or environmental parameters. The computer program then informs a user of the results in real-time via electronic means (i.e., email, text, etc.).

Figure 4:
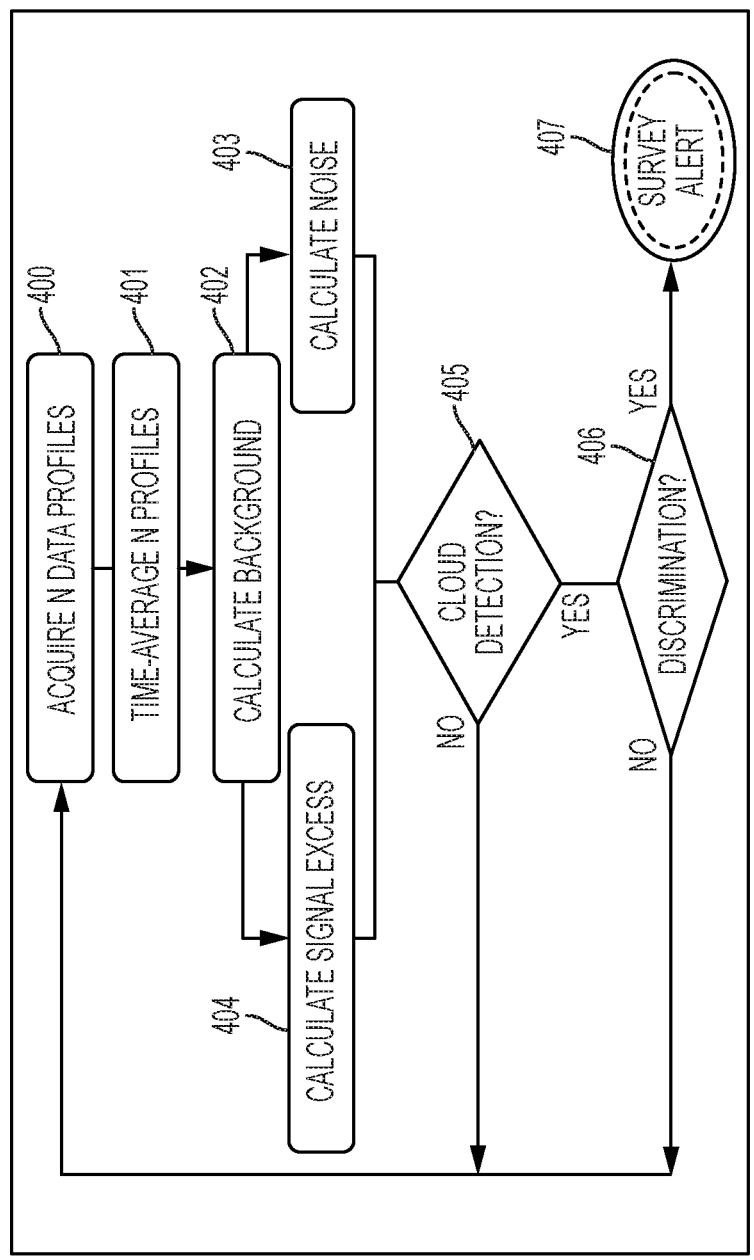
FIG. 4 is a flow chart of the computer software analytical method steps in detecting particles using the Lidar instrument, according to one embodiment consistent with the present invention.

As shown in FIG. 4, more specifically, the computer software program of the data electronics 110 of the Lidar instrument 100 first acquires "N" data profiles from the detection of the particles in step 400. Each Lidar data profile is presented as the signal counts vs. range (meters) (i.e., two data entries). In step 401, the program time-averages the "N" profiles, and then calculates the background or environmental parameters in step 402.

In step 403, the computer program calculates noise, and in step 404 calculates the signal noise excess. Using these calculations, the computer program can then determine the aerosol cloud in step 405, and the particles detected therein. If no cloud with particles is detected, then the computer program reverts to acquiring more Lidar data profiles in step 400.

If an aerosol cloud of bio-signatures is detected in step 405, then in step 406, the computer program discriminates between the particles detected, by comparing the bio-signatures against a computer database of known biological and non-biological or environmental signatures to attempt to identify the particles. In one embodiment, if a predetermined biological or non-biological signature is identified, or an unknown signature is detected, for example, then the computer program may issue a survey alert and inform the user in real-time, in step 407. Various degrees of alert can be preprogrammed to inform the user of the significance of the discovery.

In one exemplary embodiment, the Lidar instrument 100 of the present invention includes ground level environmental parameters of an extraterrestrial planet atmosphere (i.e., Mars), which are stored in the computer database, and which compares the particles detected to any biological or non-biological indicators detected by the Lidar instrument 100, such as Kaolin clay and amino acids.

In this exemplary embodiment, Kaolin clay and JSC Mars-1a (Martian regolith composition) are used, and are minimally fluorescent environmental targets (i.e., indicating fertile soil for past or existing Earth-like life on Mars). These targets represent a Martian aerosol environment dominated by sand of a mineral origin. *Bacillus globigii* (a species of *Bacillus* found in soil and in decomposing organic matter) is a weak fluorescence bio-indicator signature, suitable to estimate the limit of detection of the Lidar instrument 100 of the present invention.

In another exemplary embodiment, bio-indicators which indicate life, such as amino acids (i.e., tyrosine and tryptophan), may be detected by their weak fluorescence of proteins, and discriminated from interferents such as Kaolin clay. When receiver operational characteristic curves are plotted for the amino acid detected, and compared with the data for the Kaolin clay in the environment (i.e., the bio-discrimination space), the probability density functions show that the amino acid (i.e., tyrosine) has a higher peak value and there is minimal overlap with Kaolin clay. In other words, the detected bio-signatures are clustered in the bio-discrimination space and separated from non-biological signatures. Thus, false positive detection of bio-signatures is expected to be minimal.

In one embodiment, the Lidar instrument 100 of the present invention can be calibrated for any bio-signature (or non-biological signature) of relevance. Further, the Lidar instrument's 100 detection probability threshold can be customized by programming the computer software to the specific target environment.

Accordingly, in one embodiment, the Lidar instrument 100 of the present invention is used to locate an aerosol cloud in a three-dimensional space, parametrize its fluorescence and particle size, report cloud detection, location and aerosol biological or non-biological discrimination results, in real-time, within a predetermined interval. The fluorescence signatures of numerous biological and non-biological indicator targets and environmental interferent materials are evaluated, and stored for comparison purposes with detected bio-signatures or non-biological signatures.

In one embodiment, the Lidar instrument 100 of the present invention is a novel instrument to detect, discriminate and locate promising regions to search for bio-signatures of extant or extinct extraterrestrial life. Development of this analytical real-time technique of remote detection and discrimination of any bio-signatures dispersed in the ground-level planetary atmosphere, or from space in a fly-by mission through an aerosol plume or cloud, will dramatically increase the probability of finding the signatures of extraterrestrial life by performing atmospheric volume scans of hundreds of meters in a radial direction around a rover or lander.

It should be emphasized that the above-described embodiments of the invention are merely possible examples of implementations set forth for a clear understanding of the principles of the invention. Variations and modifications may be made to the above-described embodiments of the invention without departing from the spirit and principles of the invention. All such modifications and variations are intended to be included herein within the scope of the invention and protected by the following claims.

What is claimed is:

1. A Lidar instrument to detect a biological signature or a non-biological signature in an extraterrestrial environment, comprising:

a transceiver having a plurality of lasers operating at 266 nm, 355 nm, and 905 nm wavelengths, and emitting laser beams at an aerosol cloud of particles in the extraterrestrial environment; and a plurality of telescopes coupled to instrument optics using optical fibers, and connected to a plurality of detectors;

wherein said laser beams excite said aerosol cloud to induce fluorescence and cause differential-wavelength elastic backscatter which produces data which is measured in real-time by said detectors to determine a type of material from the biological or non-biological signature of each of said particles, and a particle size of each of said particles;
wherein said detectors are photon-counting modules in both an ultraviolet wavelength range and a near-infrared wavelength range;

wherein each said 266 nm laser and said 355 nm laser includes a filter and a photo multiplier tube; and wherein a filter and an avalanche photodiode are disposed with said 905 nm laser.

2. The Lidar instrument of claim 1, wherein an alert is issued to a user in real-time on condition that said type of material of each of said particles indicates a predetermined biological or non-biological signature.

3. The Lidar instrument of claim 2, wherein said particle size and said type of material of each of said particles is determined by making comparisons of said data received on fluorescence, with a computer database containing biological and non-biological or environmental parameters.

4. The Lidar instrument of claim 3, wherein the Lidar instrument operates at one of ground level or from space on a fly-by mission through said aerosol cloud.

5. The Lidar instrument of claim 4, wherein said environmental parameters are ground level environmental parameters of an atmosphere of the extraterrestrial environment, and include Kaolin clay and JSC Mars 1a.

6. The Lidar instrument of claim 5, wherein the Lidar instrument includes a plurality of operational modes, including a scanning mode, and a staring mode;

wherein said scanning mode is for high-fluorescence yield of bio-indicator particle detection; and wherein said staring mode is used for low-fluorescence yield dust particle detection.

7. The Lidar instrument of claim 6, wherein the Lidar instrument is operated at one of night, during sunset, or during sunrise without looking at the Sun, or at a shaded landscape as a hard target.

8. The Lidar instrument of claim 3, wherein a signal-to-noise (S/N) performance of the Lidar instrument is higher than 1.

9. The Lidar instrument of claim 1, wherein the Lidar instrument is configured to fit in a planetary vehicle or a spacecraft.

10. A method of detecting a biological signature or a non-biological signature in an extraterrestrial environment using Lidar, comprising:

emitting a laser beam from a transceiver having a plurality of lasers operating at 266 nm, 355 nm, and 905 nm wavelengths, into an aerosol cloud of particles in the extraterrestrial environment; and providing a plurality of telescopes coupled to instrument optics using optical fibers, and connected to a plurality of detectors;

wherein said laser beams excite said aerosol cloud to induce fluorescence and cause differential-wavelength elastic backscatter which produces data which is measured in real-time by said detectors to determine a type of material from the biological or non-biological signature of each of said particles, and a particle size of each of said particles; wherein said detectors are photon-counting modules in both an ultraviolet wavelength range and a near-infrared wavelength range; wherein each said 266 nm laser and said 355 nm laser includes a filter and a photomultiplier tube; and wherein a filter and an avalanche photodiode are disposed with said 905 nm laser.

11. The method of claim 10, further comprising:

issuing an alert to a user in real-time on condition that said type of material of each of said particles indicates a predetermined biological or non-biological signature.

12. The method of claim 11, further comprising:

making comparisons of said data received on fluorescence, with a computer database containing biological and non-biological or environmental parameters, in order to determine said particle size and said type of material of each of said particles.

13. The method of claim 12, wherein the Lidar instrument operates at one of ground level or from space on a fly-by mission through said aerosol cloud.

14. The method of claim 13, wherein said environmental parameters are ground level environmental parameters of an atmosphere of the extraterrestrial environment, and include Kaolin clay and JSC Mars 1a.

15. The method of claim 14, wherein the Lidar instrument includes a plurality of operational modes, including a scanning mode, and a staring mode;

wherein said scanning mode is for high-fluorescence yield of bio-indicator particle detection; and wherein said staring mode is used for low-fluorescence yield dust particle detection.

16. The method of claim 15, wherein the Lidar instrument is operated at one of night, during sunset, or during sunrise without looking at the Sun, or at a shaded landscape as a hard target.

17. The method of claim 10, wherein a signal-to-noise (S/N) performance of the Lidar instrument is higher than 1.

18. The method of claim 10, wherein the Lidar instrument is configured to fit in a planetary vehicle or a spacecraft.

* * * * *